United States Patent
Kauvar et al.

(10) Patent No.: US 9,913,899 B2
(45) Date of Patent: Mar. 13, 2018

(54) DIAGNOSTIC MARKER FOR TREATMENT OF CEREBRAL ISCHEMIA

(71) Applicant: Shimojani, LLC, San Francisco, CA (US)

(72) Inventors: Lawrence M. Kauvar, San Francisco, CA (US); Damir Janigro, Cleveland Heights, OH (US)

(73) Assignee: Shimojani, LLC, San Francisco, CA (US)

( * ) Notice: Subject to any disclaimer, the term of this patent is extended or adjusted under 35 U.S.C. 154(b) by 0 days.

(21) Appl. No.: 14/657,777

(22) Filed: Mar. 13, 2015

(65) Prior Publication Data

US 2015/0258193 A1  Sep. 17, 2015

Related U.S. Application Data

(60) Provisional application No. 61/952,710, filed on Mar. 13, 2014.

(51) Int. Cl.

| A61K 39/395 | (2006.01) |
|---|---|
| A61K 38/49 | (2006.01) |
| A61K 38/48 | (2006.01) |
| G01N 33/68 | (2006.01) |
| C07K 16/22 | (2006.01) |

(52) U.S. Cl.
CPC ........ *A61K 39/3955* (2013.01); *A61K 38/482* (2013.01); *A61K 38/49* (2013.01); *C07K 16/22* (2013.01); *C12Y 304/21068* (2013.01); *C12Y 304/21073* (2013.01); *C12Y 304/24029* (2013.01); *G01N 33/6893* (2013.01); *G01N 2333/4727* (2013.01); *G01N 2800/2871* (2013.01); *G01N 2800/52* (2013.01)

(58) Field of Classification Search
None
See application file for complete search history.

(56) References Cited

U.S. PATENT DOCUMENTS

| 6,884,591 B2* | 4/2005 | Janigro ................ G01N 33/574 435/7.1 |
|---|---|---|
| 7,144,708 B2* | 12/2006 | Janigro .............. G01N 33/6896 435/7.1 |
| 8,652,476 B2* | 2/2014 | Shimohata ............. C07K 16/22 424/130.1 |
| 2005/0130230 A1 | 6/2005 | Davalos et al. |

FOREIGN PATENT DOCUMENTS

WO    WO -11/013668    2/2011

OTHER PUBLICATIONS

Walter et al., "Diagnosis and treatment of patients with stroke in a mobile stroke unit versus in hospital: a randomised controlled trial," Lancet Neurol (2012) 11:397-404.
Kanazawa et al., "Inhibition of VEGF signaling pathway attenuates hemorrhage after tPA treatment," J Cereb Blood Flow Metab (2011) 31:1461-1474.
Herrmann et al., "Release of glial tissue-specific proteins after acute stroke: A comparative analysis of serum concentrations of protein S-100B and glial fibrillary acidic protein," Stroke (2000) 31(11):2670-2677.
International Search Report and Written Opinion for PCT/US15/20561, dated Jun. 17, 2015, 10 pages.

* cited by examiner

*Primary Examiner* — Olga N Chernyshev
(74) *Attorney, Agent, or Firm* — Morrison & Foerster LLP

(57) ABSTRACT

Identification of candidates for treatment and treatment of subjects experiencing cerebral ischemia wherein the treatment employs a thrombolytic or thrombectomy agent and an inhibitor of vascular endothelial growth factor (VEGF) receptor-mediated signal transduction are determined by testing the blood of a patient for total S-100B or for S-100BB as a marker of blood brain barrier integrity.

3 Claims, 3 Drawing Sheets

Prior Art

DIAGNOSTIC MARKER FOR TREATMENT OF CEREBRAL ISCHEMIA

CROSS-REFERENCE TO RELATED APPLICATIONS

This application claims priority from U.S. provisional application 61/952,710 filed 13 Mar. 2014. The contents of these documents are incorporated herein by reference.

TECHNICAL FIELD

The present invention relates to methods to identify patients experiencing cerebral ischemia who will benefit from treatment employing a thrombolytic agent and an inhibitor of vascular endothelial growth factor (VEGF) receptor-mediated signal transduction and treatment of said subjects in an appropriate treatment window. These methods are based on testing the blood of a patient for levels of a marker for blood-brain barrier (BBB) integrity.

BACKGROUND ART

The present invention provides an assay which will increase the therapeutic value of stroke treatment by identifying patients who can benefit from such treatment in a more reliable and timely manner, which is expected to greatly increase the number of patients considered eligible for this treatment by at least five-fold.

PCT application PCT/JP2010/062631, published as WO2011/013668 and filed as a continuation-in-part in the United States as U.S. Ser. No. 13/359,281, now U.S. Pat. No. 8,652,476 describes methods to treat cerebral infarction or ischemia in humans by administering a combination of a thrombolytic intervention and an inhibitor of VEGF-receptor mediated signal transduction during the acute stage of the cerebral ischemic event which is considered to be within 6 hours after the onset of the cerebral infarction, with the combination providing reduced toxicity as compared to thrombolytic intervention alone. Determining the time of the onset of cerebral infarction, however, is difficult as typically the subject is not under medical supervision at that time. In addition, for cerebral infarction specifically, the treatment window appears to be critical. Presence of a disrupted BBB in a subject with embolic stroke is a risk factor for hemorrhage after thrombolysis. It is thus reasonable in hindsight that the levels of a blood-brain barrier disruption promoting factor, such as VEGF, correlates inversely with thrombolytic safety.

A variety of thrombolytic inventions is described in the literature as is a variety of methods to inhibit VEGF-receptor mediated signal transduction. For example, the thrombolytic invention may include a plasminogen activator such as tissue plasminogen activator (tPA), urokinase, streptokinase or their analogs, other plasminogen activators such as that derived from vampire bats, or mechanical destruction or removal of the embolus. The inhibitor of VEGF-receptor mediated signal transduction may be a specific binding partner for VEGF or VEGF-R or a compound that inhibits the release of VEGF from platelets or a compound that disrupts signal transduction from activated VEGF-R.

The above documents, and all others cited herein are incorporated by reference.

Thrombolytics like tPA are currently used in only a few percent of stroke patients due to the toxicity risk, which is exacerbated when given more than 3 hours after the stroke. With adjunct therapy available to reduce the toxicity of tPA, the patient population expected to benefit from such treatment is considerably increased. This combination of interventions, however, according to the PCT document depends on clock time from a starting point that is notoriously difficult to determine. It would be useful to have instead a method to determine the suitable treatment window that relies on physiological status.

Moreover, the severity of the stroke is proportional to the degree of disruption of the blood brain barrier (BBB). The most severe strokes also benefit the most from thrombolytic therapy. In light of the risk of toxicity from plasminogen activators, therefore, their use is currently avoided for mild strokes, even though full clot dissolution is easier to achieve in such cases. Thus, measuring degree of disruption of the BBB provides a combined measure of stroke timing and severity, and it is considered that more severe strokes warrant the risks associated with this treatment. Currently, this assessment is made following a CT scan at the hospital, resulting in substantial delay in treatment compared to the optimal early administration of thrombolytic agents. A measure suitable for assessing BBB disruption by a point of care assay feasible to use in the ambulance is provided by the present invention. In pilot studies using an ambulance equipped with a portable CT scanner to reduce the delay in diagnosis, substantial reduction in the time required to select thrombolytic intervention was achieved over standard of care; Walter, S., *Lancet Neurology* (2012) 11:397-404. However, the high cost of a portable CT scanner makes it important to develop a simpler point of care diagnostic for stroke severity.

DISCLOSURE OF THE INVENTION

According to the present invention, the combination treatment described in the above-referenced applications should be administered only in cases where the severity of the stroke is sufficient to warrant the risk of treatment with a thrombolytic agent which may cause hemorrhaging even if a preventative as described above—i.e., an inhibitor of VEGF-R signal transduction—is administered as well. In addition, the administering should be during the time period after the cerebral ischemic event when the integrity of the blood-brain barrier (BBB) has been disturbed and up to the time of the maximum level of disruption. Presently, the severity (indeed the presence of) a stroke or cerebral infarction and a suitable time for administration of treatment has been determined only after arrival at a hospital and performance of a CT scan to conclude that there was a stroke severe enough to justify the risk associated with thrombolysis. The present invention offers determination of both desirability and timing of administration with thrombolytic agents in an expeditious manner that can be administered prior to arrival at the hospital, for example, in an ambulance. It is estimated that with this improved diagnostic method, the use of thrombolytic agents in patients resulting in desirable therapeutic effects would increase from less than 5% of putative stroke patients to more than 25% of them.

Determination of both severity and the period of disturbance of this BBB integrity can be accomplished by employing a marker for this integrity that is present in the blood. A suitable marker is described in a paper by Marchi, N., et al., *Res. Neurol. Neurosci.* (2002) 20:1-13, in their corresponding patents U.S. Pat. No. 7,144,708 and U.S. Pat. No. 6,884,591 and their later PCT application published as WO2012/154889. These documents describe methods for diagnosing blood-brain barrier permeability in a subject comprising using as a marker total the level of S-100B or its homodimer wherein elevated levels of S-100B or its homodimer indicate BBB permeability.

While it is not made explicit in these documents, it appears that what is referred to as S-100B in the two issued U.S. patents in reality refers to the total amount of S-100B in the peripheral blood, regardless of its presence any monomeric or dimeric forms. Apparently, the S-100B may exist as a monomer, but primarily it is present in brain as its homodimer (S-100BB) and its heterodimer (S-100AB). From the description in the U.S. patents, it appears that what is being measured is the total of all of these forms, rather than measurement of the S-100BB homodimer specifically.

In the subsequent PCT publication, this is made somewhat more clear, and it is disclosed that it is preferable to measure specifically the S-100BB homodimer as this is the major form that is liberated into the blood by disruption of the BBB. This is discussed in the above PCT publication on page 26, beginning at line 26, to page 27, line 14, which discusses the two types of antibodies used and on page 29, line 25-page 30, line 16, as well as page 33, lines 6-20. However, detection of total S-100B is also recognized means to determine the integrity of the BBB. As taught in the PCT publication referenced above, these values are quite close.

An earlier issued U.S. patent, U.S. Pat. No. 6,555,327 describes monoclonal antibodies with specificities varying among the various dimers formed from the S-100 protein in the brain. One of these antibodies, S10 recognizes an epitope accessible only in S-100BB, but not accessible in S-100AA or S-100AB. Other antibodies recognize S-100AB only or combination of S-100BB and S-100AB. As noted below, monoclonal antibodies specific for S-100BB are available commercially.

S-100BB is secreted from some astrocytes. It is a calcium binding protein whose normal level in peripheral blood is extremely low. Use of the level of total S-100B or the homodimer as a marker permits selection of patients for whom the benefit of the combination treatment with thrombolysis and VEGF-inhibition outweighs the risk of induced hemorrhage associated with thrombolytic treatment. That is, a refined assessment of whether a thrombolytic treatment should be administered at all is made practical by measuring S-100B or the homodimer in the peripheral blood as a marker of severity. High levels of this marker indicate a more severe level of infarction where the BBB has been seriously affected. Thus, such treatment is indicated when the levels of total S-100B or S-100BB are present in peripheral blood above a threshold level indicative of the damage to the BBB. The exact threshold level depends in part on the nature of the assay, but also on the subject. The threshold level will vary with age, ethnicity and gender. To be certain of its significance, the threshold value should be determined by that obtained in a similar cohort known to be stroke victims matched by age, ethnicity and gender. Results of prior assays on such groups may be used in such a determination. In any event, however, levels above 0.12 µg/mL would clearly be a sufficient threshold indicator of severe BBB disruption regardless of these variables.

In addition, the timing of the treatment can be determined more reliably by ensuring that the thrombolysis is administered during the time wherein the BBB loses its integrity. This is characterized by the foregoing levels of total S-100B or the S-100BB homodimer in peripheral blood or, alternatively, two or more measurements of these levels may be obtained at slightly different times (e.g., 2 minutes apart, 5 minutes apart or 10 minutes apart) to verify that the levels of 5-100B or specifically the homodimer are continuing to increase. Earlier administration of the thrombolytic, combined with the decreased risk of hemorrhage from concomitant administration of an anti-VEGF agent, substantially expands the proportion of patients appropriate to treat above that currently which is well under 5% of all stroke patients. The use of S-100B as a marker addresses both severity and timing issues. As a marker tightly linked to BBB damage, it is particularly appropriate to use in selecting anti-VEGF treatment as that treatment directly addresses the BBB damage. Other proposed stroke markers, such as matrix metalloproteases, are not so tightly linked.

Thus, the invention is directed to a method to reduce neuronal damage caused by a cerebral ischemic event in a human patient comprising administering to said patient during a period of BBB integrity loss resulting from said event as measured by blood levels of total S-100B or the homodimer, effective amounts of a thrombolytic or mechanical thrombolysis intervention and an inhibitor of VEGF-R-mediated signal transduction. The decision to do so is based on the results of measuring these levels in the peripheral blood of said patient, and if a level of above the threshold discussed above is found, administering said effective amounts of a thrombolytic or thrombectomy intervention and an inhibitor of VEGF-R-mediated signal transduction to said patient.

The preferred period of administration is during the time the patient is undergoing BBB integrity loss as determined by measuring the level of total S-100B or of S-100BB in the peripheral blood of said subject, wherein an elevated level of S-100B or S-100BB above the threshold, e.g. of 0.12 µg/mL indicates said BBB integrity loss, and wherein the treatment window extends from the time of an initial rise in total S-100B or of S-100BB concentration to the time a maximal value for that concentration is obtained. The time during which BBB integrity is being lost is indicated by the above-mentioned levels of S-100B or its homodimer in peripheral blood or, alternatively, by measuring the levels of these proteins at different times to determine whether they continue to increase. The interval between measurements is typically 1 to 15 minutes, or 2 to 10 minutes.

While the focus of the present invention is on the marker S-100B or specifically the homodimer form thereof, other markers of blood brain barrier disruption are known in the art, and can be used in combination with the assays of the invention. Thus, it is also known that elevated levels of UCHL-1 in the peripheral blood are diagnostic of BBB disruption. Puvenna V., et al., (2014) *PLoS ONE* 9(5): e96296. Measurement of such additional markers in combination with measurement of total S-100B or of S-100BB specifically may be helpful in improving the prognostic value of the assessment.

The invention also is directed to kits that contain reagents for determining S-100B or its homodimer and to containers of therapeutic agents in compositions or materials to provide thrombolytic or thrombectomy intervention in conjunction with inhibitors of VEGF-R-mediated signal transduction. If an additional marker is used, assay materials for this additional marker may also be included in the kit.

MODES OF CARRYING OUT THE INVENTION

Because the present invention provides a portable, efficient, and accurate assay for BBB disruption, and thus, an evaluation of desirability and timing of treatment, the present invention offers improvements in relation to the treatment described in the above-referenced WO2011/013668 which is incorporated herein by reference. Suitable thrombolytic or thrombectomy materials and reagents and agents for disrupting VEGF-R signaling are set forth in detail in that document and need not be repeated here. These improvements include determining whether to treat with a thrombolytic agent, at all, based on the severity of the stroke or cerebral infarction, and determining the suitable time for administering the treatment. Because thrombolytic treatment is inherently dangerous and can cause hemorrhaging no matter when it is administered, it is desirable to treat only those patients where the severity of the stroke merits taking this risk. Severity is directly related to destruction of the blood-brain barrier (BBB) and thus, the severity of the stroke can be determined by markers that indicate the level of the integrity of the BBB. In the present invention, total S-100B or the homodimer thereof is used as a marker for the level of BBB loss of integrity. Use of these markers as diagnostic of BBB integrity is known in the art; their use to determine desirability of and timing of the herein-described intervention in treating cerebral ischemia is not.

Figure 1:
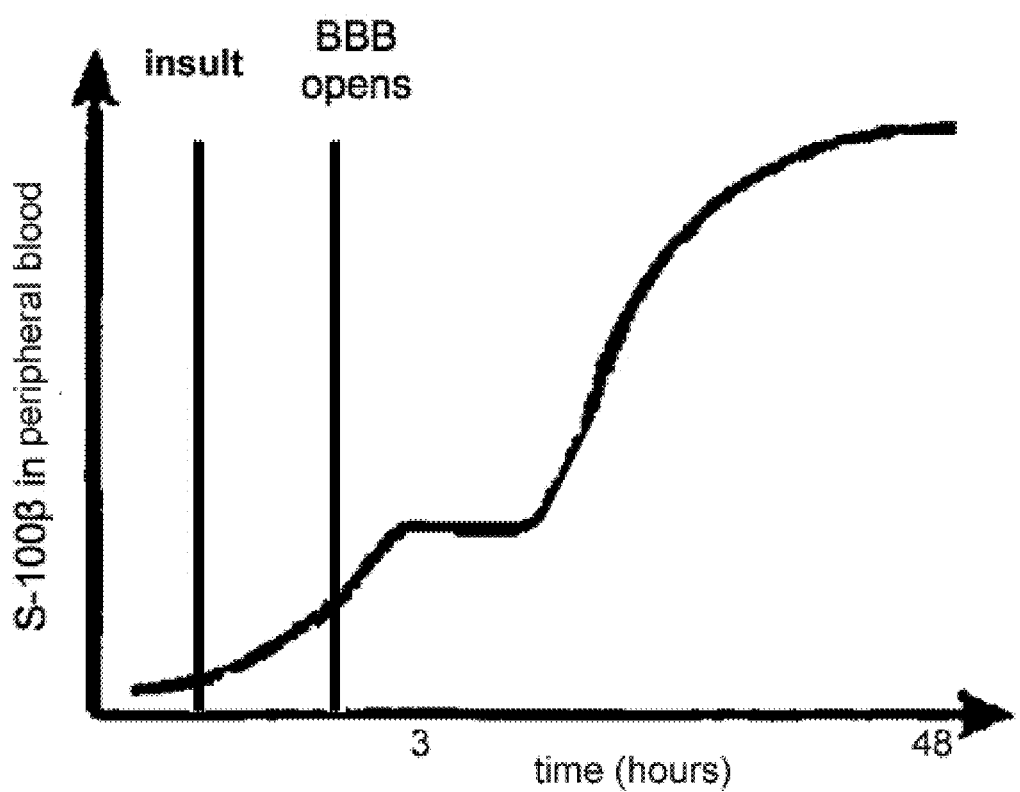
FIG. 1 is a graph showing the level of disruption of the BBB as determined by the concentration of total S-100B in serum subsequent to an ischemic event as described in the prior art and is reproduced from U.S. Pat. No. 6,884,591.

U.S. Pat. Nos. 6,884,591 and 7,144,708, specifically incorporated herein by reference with respect to conduct of the assays described, describe assays for the behavior of BBB integrity subsequent to cerebral ischemia. An initial elevation of the level of S-100B occurs in the blood, followed by an additional, more dramatic increase which indicates neuronal damage. This is shown in FIG. 1 drawn from the '591 patent. The appropriate treatment window for administration of the thrombolytic intervention and the inhibitor of VEGF-R signal transduction is the time period between the initial smaller increase of S-100B and the higher plateau reached subsequently. This interval is roughly between 3 hours and 48 hours on the clock.

As outlined in the '591 and '708 patents, measurement of S-100B in the blood (or plasma or serum) has the advantage that its levels are normally very low or undetectable in blood. According to these documents, normal levels are only 0.055 µg/l in men and 0.048 µg/l in women. (In contrast, in cerebrospinal fluid the values are 1.9 µg/l for men and 1.5 µg/l for women.) The manner of assessing S-100B includes many possibilities known in the art, such as immunological assays, including sandwich assays, Western blot, mass spectrometry, flow cytometry, and the like. Particularly preferred methods are those appropriate for high sensitivity point of care assays such as localized surface plasmon resonance, or surface enhanced Raman spectroscopy. The range of S-100B levels that is readily detectable, again according to these documents, is 0.001 µg/l to about 1 mg/l. Thus, increases above the normal level can readily be measured.

Some improvements in methods to assess the relevant levels of the S-100B protein as a measure of loss of BBB integrity are reported by the same authors in PCT publication WO2012/154889, also incorporated herein by reference. As noted, the assay may be improved by selectively detecting a level of the homodimer of S-100B (S-100BB) and comparing its level to the level of S-100BB in a control. (As noted above, an alternative dimer is formed by S-100B with a related protein, S-100A (S-100AB) which is less relevant.) The applicants in the '889 publication state that S-100BB detection is superior to S-100B detection per se as an indicator of BBB permeability. A number of antibodies, some commercially available, for detecting S-100BB are also disclosed.

A specific assay that is capable of detecting only the homodimer is found in this PCT publication in Example 2 on page 35 which is illustrated in FIG. 5 thereof. As shown, the assay—a commercially available Proximity Ligation Assay (PLA)—involves amplification of a complementary double-stranded nucleotide sequence coupled to antibodies binding the 0 sequence of each monomer in the homodimer. As defined herein, and as apparently defined in these referenced documents, S-100B refers to the total concentration of all three forms of this protein including the monomer, the heterodimer and the homodimer. Methods specifically to distinguish the homodimer from the total or from the monomer should be possible using Western blot; the apparent failure of these documents to do so may reflect the preponderance of the homodimer as the form that exits the BBB when it is disrupted.

While analysis of total forms involving S-100B—i.e., both heterodimer and homodimer as well as monomer—are useful, the specificity and sensitivity of the test is improved by analyzing specifically for the homodimer. Antibodies for either specificity are commercially available, for example, from Fujirebio Diagnostics, and the variety of antibodies available is illustrated in the following table:

TABLE 1

| MAb | Isotype | Form | Prod. No. | Comments |
| --- | --- | --- | --- | --- |
| S10 | IgG1 | Purified | 701-01 | Epitope specific for S100BB * |
| S21 | IgG1 | Purified | 703-01 | S100B epitope exposed in both S100BB and S100A1B |
| S23 | IgG1 | Purified | 704-01 | S100B epitope exposed in both S100BB and S100A1B |
| S35 | IgG1 | Purified | 706-01 | Epitope specific for S100A1B * |
| S36 | IgG1 | Purified | 707-01 | S100B epitope exposed in both S100BB and S100A1B |
| S53 | IgG1 | Purified | 708-01 | S100B epitope exposed in both S100BB and S100A1B |

* Covered by U.S. Pat. No. 6,555,327

The website for the commercial source is fdi.com/us_home/products/antibodies/s100.html.

A preferred treatment in all cases is the combination of a thrombolytic agent or mechanical from biolysis in combination with an inhibitor or VEGF-receptor signal transduction. However, in some instances, the thrombolytic treatment itself may be sufficient if administered sufficiently early in the course of the stroke. Nevertheless, it is much preferred to use the combination of agents since the inhibitor of VEGF-receptor signal transduction would in any case assist in ameliorating the danger of hemorrhage that would result from thrombolytic.

The agents employable to effect thrombolysis and to effect inhibition of VEGF-R signal transduction are described in great detail in the above-referenced WO2001/

013668. For example, with respect to inhibitors of VEGF-R-mediated signal transduction, such inhibitors include, for example, inhibitors that decrease the binding of VEGF to VEGF-R, inhibitors that inhibit the release of VEGF from platelets, inhibitors that interact with a component of the VEGF-R signaling pathway, inhibitors that interact with an enzyme that modifies a component of the VEGF-R signaling pathway, and inhibitors that decrease the production of at least one of VEGF and VEGF receptor.

Specific binding partners include a receptor or ligand that binds specifically to at least one of VEGF and VEGF receptor, such as antibodies, peptides, peptidomimetics and aptamers.

"Antibodies" can encompass Fab fragments, single chain Fv constructs, bi-specific constructs in which one Fc is linked to two different Fab fragments, and similar constructs thereto. The antibodies are minimally antigenic in humans and thus may be human by sequence (from a transgenic animal expressing a human antibody repertoire or a recombinant library of human antibody genes) may be humanized or may be isolated from a human or may be chimeric. Likewise, reduced size (low-molecular-weight) antibodies (nanobodies) such as antibodies (naturally occurring variants) found in camels or sharks are also useable.

Antibody mimics include families of proteins based on scaffolds such as: fibronectin, transferrin, glutathione transferase, lens crystallin. Other mimics include small peptides, peptide mimics (for example, incorporating beta amino acids, or D-amino acids, or chemical crosslinkers to increase conformational stability, as well as non-peptide binding agents such as nucleic acid based aptamers.

"Antibody mimics" refer to all such binding agents achieving the same functionality as an antibody, and usable in place of an antibody in the present invention.

The antibodies may be polyclonal or monoclonal and may comprise only fragments and may be recombinantly produced. In addition to antibodies and mimics, binders to the VEGF-R may be analogs of VEGF that bind to the receptor but do not agonize it. A variety of VEGF receptor signaling peptide inhibitors that are available is set forth in paragraph 96 of the above-referenced PCT publication WO2011/013668 specifically incorporated herein by reference. Also therein described are inhibitors that decrease the production of either VEGF or VEGF-R as set forth in paragraphs 99-104.

With respect to thrombolytic agents and interventions, various plasminogen activators could be employed such as tissue plasminogen activator (tPA) or a derivative thereof, urokinase, streptokinase, single-chain urokinase-type plasminogen activator (uPA), desmoteplase (derived from vampire bat plasminogen activator), and other proteases acting on fibrin. Other agents known to cleave fibrin are also used in the present invention. These may be used alone or in combination. Mechanical thrombolysis or clot removal is also useable to treat the primary ischemic event.

Specific examples of derivatives of tPA include: tPA derivatives having the same amino acid sequence of the tPA except that part of the amino acids are substituted (e.g., derivatives known in the art, such as monteplase, pamiteplase and reteplase); and tPA derivatives modified with a sugar chain and having the same amino acid sequence of tPA except that part of the amino acids are substituted (e.g., tenecteplase and lanoteplase).

In addition to thrombolytic agents, mechanical methods for thrombolysis or clot removal may also be employed in lieu of or in addition to such agents.

The inhibition of the VEGF-R signal transduction is effective to counteract the negative effects of the thrombolytic intervention which contribute to edema formation and hemorrhagic transformation (HT) as described in WO2011/013668. (Other combinations to prevent these effects have been suggested, for example, by Ishrat, T., et al., Cur. Pharm. Des. (2012) 18:3677-3684. Such combinations do not include inhibition of VEGF-R signal transduction as other reports have found negative indications for this treatment reflecting the importance of elevated VEGF in the later tissue repair phase of recovery.) Nevertheless, neither this paper nor the '668 define a treatment window that is appropriate based on a physiological clock.

EXAMPLES

The following examples illustrate but do not limit the invention.

Example 1

Assay to Evaluate Combined Administration of tPA and Anti-VEGF Antibody as a Function of Treatment Window A cerebral infarction rat model is disclosed in the above-referenced WO2011/013668. Briefly, a thrombus is formed by coagulating autologous blood from rats and thrombin as a gel in a polyethylene tube catheter. This is allowed to stand overnight and cut to have a length of 1 mm. The thrombus is injected from the external carotid artery into the middle cerebral artery of the rat model under anesthesia with halothane. Cerebral blood flow is measured before and 30 minutes or 24 hours after injection of the thrombus. Animals exhibiting a cerebral blood flow lower than 50% of that measured before injection of the thrombus are used as models in the experiments.

After injection of the thrombus, BBB status is assessed by comparing the serum S-100B level as a function of time as compared to the S-100B level measured prior to injection of the thrombus.

The rats were divided into experimental groups as listed below. Each experimental group received 100 µg of rabbit anti-rat VEGF antibody IgG (Rb-222) (Lab Vision-Neo-Markers) together with tPA alteplase (marketed as Activase® by Mitsubishi Tanabe Pharma Corporation) injected for 30 minutes into the femoral vein at 10 mg/kg, 10% bolus administration in 90% drip infusion.

Sham operation group; n=3
tPA at 4 hours+control IgG; n=5
tPA at 4 hours+RB-222 (anti-VEGF); n=5

For each animal, 50 µL of blood were drawn at the following times:
pre-ischemia (2-24 hours before)
just prior to tPA treatment (4 hours post-ischemia)
10 hours post-ischemia
24-48 hours (at time of sacrifice)

Blood was collected into BD Microtainer tubes catalog #365967 (silicon coated, with clot activator), and the tubes inverted S-6 times to allow the blood to clot thoroughly. After 30 minutes, the blood was centrifuged at 2,000 rpm for 10 min and the serum carefully separated. The level of S-100B in the serum was then measured by ELISA.

Figure 3:
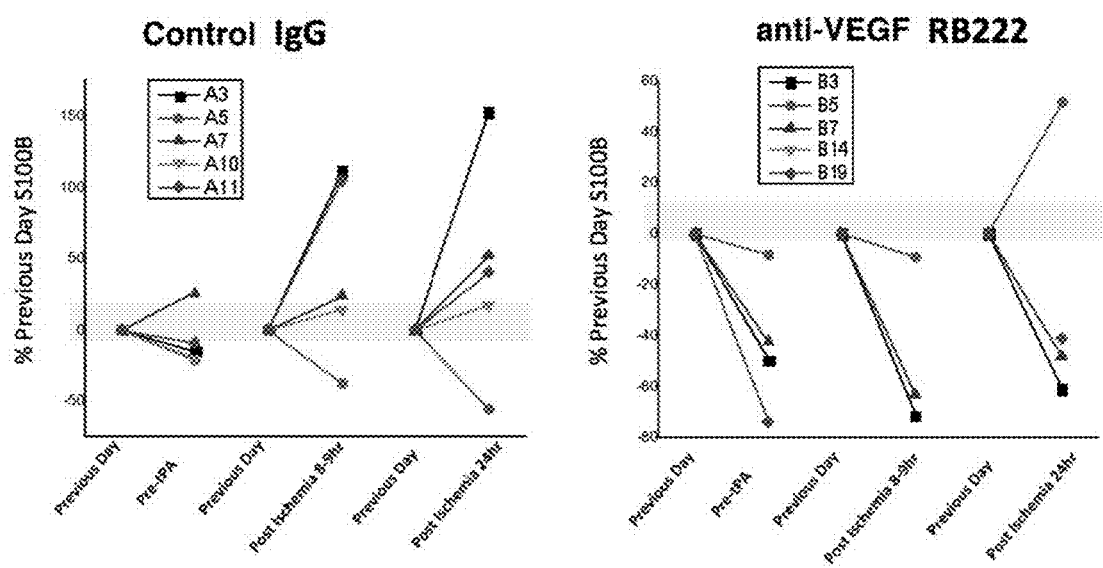
FIG. 3 shows serum S-100B levels in individual rats with an artificially created ischemic stroke treated with a control antibody or with an antibody against VEGF. Treatment with anti-VEGF markedly reduced the level of S-100B consistent with prior studies showing improved outcomes for this treatment.

As shown in FIG. 3, the anti-VEGF treatment markedly reduced the S-100B level normalized against the level in the same individual rat prior to the induced stroke. The graphs show S-100B levels for each control rat (A) and each rat administered RB-222 (B). The efficacy was seen at both time points (3-9 hours and 24 hours following the induced stroke with 4 out of 5 rats showing decreased S-100B in the anti-VEGF group compared to only one in the control group.

Example 2

Measurement of VEGF and S-100B in Human Stroke Thrombus Samples

Currently, tissue-plasminogen activator (tPA) is the only drug used to dissolve intra-arterial clots, helping to restore cerebral blood flow. Other interventional strategies include the use of tools that mechanically disrupt and remove intra-arterial clots. A total of 30 patients were enrolled, 15 of whom were classified as hemorrhagic by clinical criteria including time since stroke onset, age, stroke severity, and by radiographic evaluation using CT and MRI and thus selected for endovascular recanalization procedure. The 18 L microcatheter MERCI® clot retrieval system was advanced over a 0.014" microwire to the thrombus. The microwire was removed and the MERCI® retrieval device advanced to the thrombus and deployed. The clot was then extracted as a part of routine clinical care. During extraction, approximately 20 mL of blood was aspirated. The extracted thrombus and aspirate are normally discarded, but were in this study saved for analysis. Peripheral blood samples (~30 mL) were also collected from a femoral arterial catheter already placed in the patients as part of the standard procedure to access the artery. After separating plasma and white blood cells, the samples were assayed for both VEGF and S-100B levels by ELISA assays.

Figure 2A:
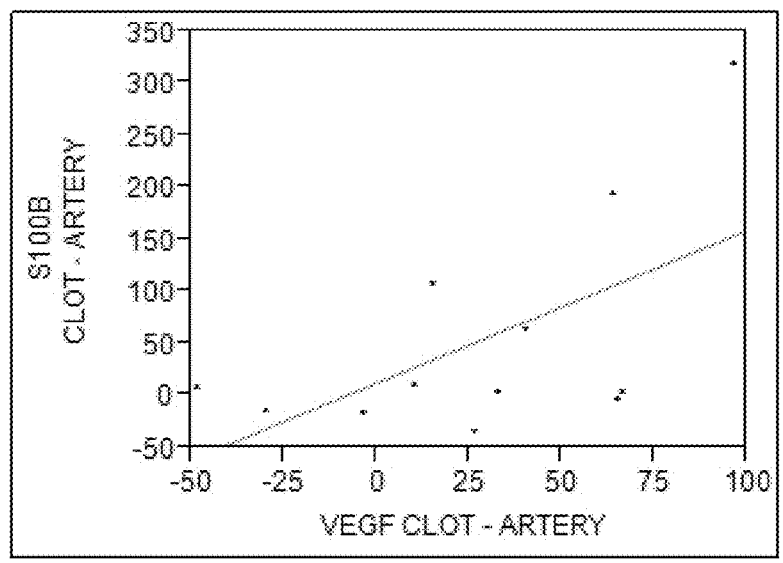
FIG. 2A shows that S-100B level in extracted thrombus from human stroke patients treated by mechanical thrombolysis is correlated with the VEGF level in the thrombus. Both were normalized by subtracting peripheral blood level.
Figure 2B:
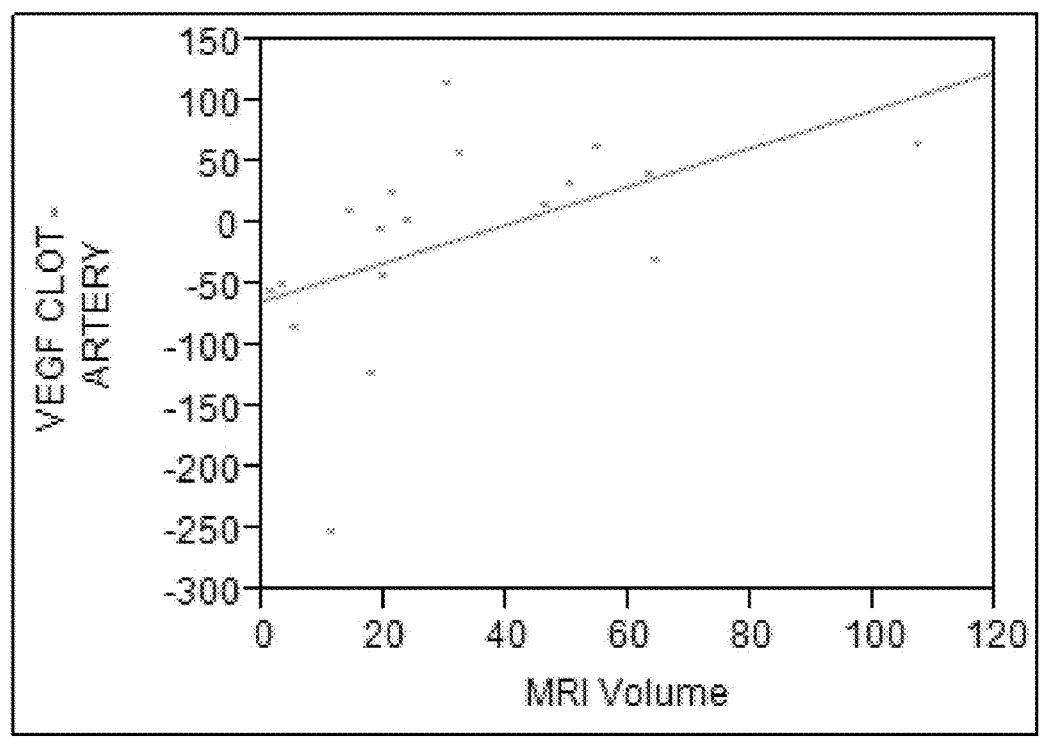
FIG. 2B shows that the normalized VEGF level is well correlated with stroke severity defined by an MRI scan.

Because the basal level of VEGF varies widely among individuals, the thrombus levels of VEGF were normalized by subtracting the corresponding intra-patient blood sample VEGF level. Similar normalization was conducted for S-100B, although for that analyte, the background blood level was very low. As shown in FIGS. 2A and 2B, there was a strong correlation between S-100B level and VEGF level in the thrombus samples. There was also a strong correlation between VEGF level and stroke severity as defined by MRI.

These results are consistent with published data on S-100B as a marker of stroke severity. For example, *Neurol. Neurochir. Pol.* (2005) 39:310-317 (article in Polish, abstract in English) reported on a cohort of 67 patients, 14 of whom were classified as having hemorrhagic stroke by CT scan. The S-100B level in blood at 24 hours (the first time point studied) was well correlated with infarct volume for severe strokes, but below the threshold of detection for mild strokes (and peaking at 3 days for the milder strokes). In a similar study of 275 patients, 45 of whom were classified as hemorrhagic (*Stroke* (2007) 38:2491-2495), an S-100B value in the highest quintile corresponded to an Odds Ratio for HT of 2.87 (95% CI: 1.55 to 5.32; P=0.001) in univariate analysis and of 2.80 (1.40 to 5.62; P=0.004) after adjustment for age, sex, symptom severity, timespan from symptom onset to hospital admission, vascular risk factors, and storage time of serum probes. Importantly, in this 2007 study, S-100B in the acute stage did not show statistically significant correlation with final outcome, but since the patients received diverse treatments, that result is not relevant to the use of S-100B as a marker for selecting patients expected to benefit from anti-VEGF treatment, particularly in conjunction with tPA which exacerbates BBB leakiness. Similarly, a review of multiple S-100B studies concluded that it is not suitable as a marker of stroke in general, but is useful as a surrogate marker for cerebral damage (*Cerebrovasc. Dis.* (2009) 27:295-302). The use of tPA combined with an agent to ameliorate tPA toxicity by blocking VEGF signaling is most appropriate for patients with more severe cerebral damage. The prior literature thus supports use of S-100B as a marker for selecting patients to receive this combination therapy.

The invention claimed is:

1. A method to reduce neuronal damage caused by a cerebral ischemic event in a human patient said method comprising:
   measuring the level of total S-100B or of S-100BB in the peripheral blood of said patient, and
   if a level of total S-100B or of S-100BB above a threshold level of 0.12 µg/ml is found,
   (a) administering an effective amount of a thrombolytic agent or performing a thrombectomy intervention to remove a thrombus, and
   (b) administering an effective amount of an inhibitor of vascular endothelial growth factor receptor (VEGF-R)-mediated signal transduction to said patient
   wherein the inhibitor of VEGF-R mediated signal transduction is an antibody or antigen-binding fragment thereof that specifically binds to vascular endothelial growth factor (VEGF) or binds to VEGF-R and is antagonistic thereto or is selected from the group consisting of SU1498, SU5416, cediranib (AZD2171), sunitinib (SU11248), vatalanib (PTK787/ZK222584), sorafenib, and pazopanib (GW786034B).

2. The method of claim 1 which further includes verifying that steps (a) and (b) are conducted during the time blood brain barrier (BBB) integrity is being lost by measuring the level of total S-100B or of S-100BB at a first time point prior to conducting steps (a) and (b) and a second time point during or after conducting steps (a) and (b) wherein the second time point is within 15 minutes later than first time point to confirm that the level at the second time point is higher than the level at the first time point.

3. The method of claim 1 wherein in (a) an effective amount of a thrombolytic agent is administered and said thrombolytic agent comprises tissue plasminogen activator (tPA), urokinase, streptokinase, desmoteplase, or single chain urokinase-type plasminogen activator-(uPA).

* * * * *